(12) United States Patent
Dake et al.

(10) Patent No.: US 10,054,545 B2
(45) Date of Patent: Aug. 21, 2018

(54) SUPER-RESOLUTION OBSERVATION DEVICE AND SUPER-RESOLUTION OBSERVATION METHOD

(71) Applicant: NIKON CORPORATION, Tokyo (JP)

(72) Inventors: Fumihiro Dake, Kawasaki (JP); Hiroki Yazawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 15/276,397

(22) Filed: Sep. 26, 2016

(65) Prior Publication Data

US 2017/0082546 A1     Mar. 23, 2017

Related U.S. Application Data

(63) Continuation of application No. PCT/JP2015/001699, filed on Mar. 25, 2015.

(30) Foreign Application Priority Data

Apr. 1, 2014   (JP) ................................. 2014-075615

(51) Int. Cl.
  *G01N 21/64*   (2006.01)
  *G02B 21/00*   (2006.01)
  (Continued)

(52) U.S. Cl.
  CPC ....... *G01N 21/6458* (2013.01); *G01N 21/636* (2013.01); *G02B 21/0076* (2013.01);
  (Continued)

(58) Field of Classification Search
  CPC ............ G01N 21/6458; G01N 21/636; G01N 2201/0675; G01N 2201/0697;
  (Continued)

(56) References Cited

U.S. PATENT DOCUMENTS

| 2007/0023686 A1 | 2/2007 | Wolleschensky et al. |
| 2010/0006772 A1 | 1/2010 | Gugel |
| 2012/0307238 A1 | 12/2012 | Fujita et al. |

FOREIGN PATENT DOCUMENTS

| JP | 2010-506155 A | 2/2010 |
| JP | 2013-019908 A | 1/2013 |
| WO | 2011/099269 A1 | 8/2011 |

OTHER PUBLICATIONS

Jun. 23, 2015 International Search Report issued in International Patent Application No. PCT/JP2015/001699.
(Continued)

*Primary Examiner* — David Porta
*Assistant Examiner* — Faye Boosalis
(74) *Attorney, Agent, or Firm* — Oliff PLC

(57) ABSTRACT

A super-resolution observation device includes an illumination optical system that focus a first illuminating light at optical frequency $\omega_1$ and a second illuminating light at optical frequency $\omega_2$ on a region of an observation object plane; a modulation unit that modulates a property of the first illuminating light heading toward the region at a modulation frequency $f_m$; and an extraction unit that extracts a component at the optical frequency $\omega_1$ or $\omega_2$ from a light generated in the region according to the first illuminating light and the second illuminating light, the component of which the property changes at a frequency higher than the modulation frequency $f_m$.

16 Claims, 11 Drawing Sheets

(51) Int. Cl.
  *G01N 21/63* (2006.01)
  *G02B 21/08* (2006.01)
  *G02B 21/16* (2006.01)
  *G02B 21/36* (2006.01)
  *G02F 1/11* (2006.01)

(52) U.S. Cl.
  CPC ....... *G02B 21/0084* (2013.01); *G02B 21/086* (2013.01); *G02B 21/16* (2013.01); *G02B 21/367* (2013.01); *G02F 1/11* (2013.01); *G01N 2201/0675* (2013.01); *G01N 2201/0697* (2013.01)

(58) Field of Classification Search
  CPC .. G02B 21/0076; G02B 21/086; G02B 21/16; G02F 1/11
  See application file for complete search history.

(56) References Cited

OTHER PUBLICATIONS

Oct. 14, 2016 International Preliminary Report on Patentability issued in International Patent Application No. PCT/JP2015/001699.
Fujita., "Recent Developments in Super Resolution Flourescence Miscroscopy", Biophysics, vol. 50, No. 4, pp. 174-179, 2010.
Nov. 14, 2017 Office Action issued in Japanese Patent Application No. 2014-075615.

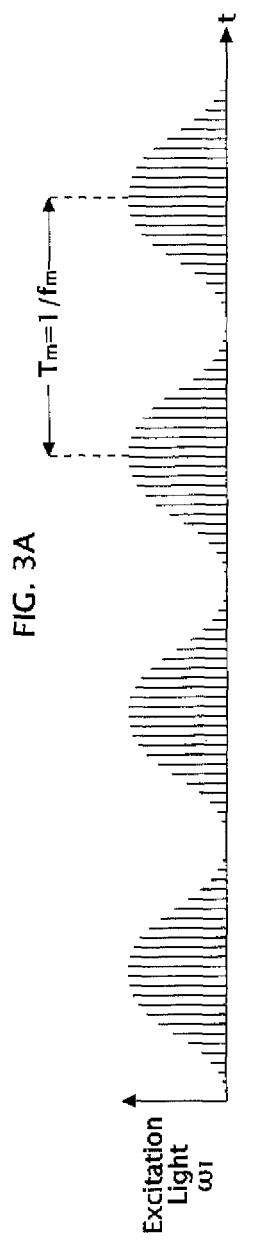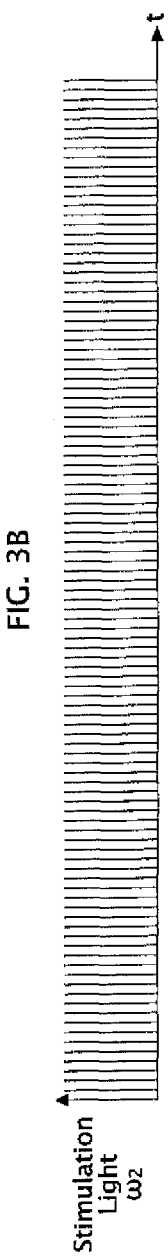
FIG. 3A
FIG. 3B

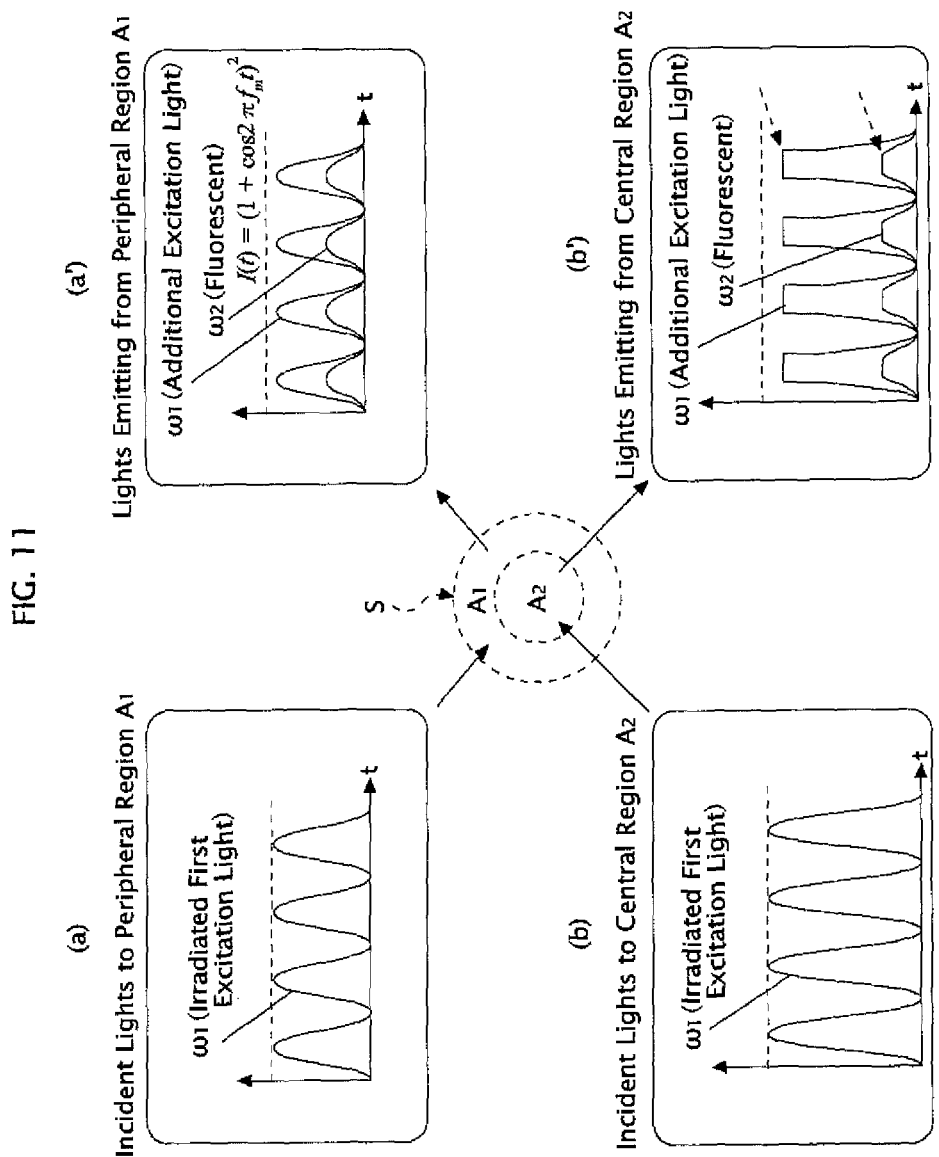

SUPER-RESOLUTION OBSERVATION DEVICE AND SUPER-RESOLUTION OBSERVATION METHOD

CROSS REFERENCE TO RELATED APPLICATION

This application is a continuation application of International Application No. PCT/JP2015/001699, filed on Mar. 25, 2015, designating the U.S., in which the International Application claims a priority date of Apr. 1, 2014, based on prior filed Japanese Patent Application No. 2014-075615, the entire contents of which are incorporated herein by reference.

BACKGROUND

1. Field

The present application relates to a super-resolution observation device and a super-resolution observation method.

2. Description of the Related Art

In recent years, in the field of bioscience, particularly, molecular biology and in the field of pathological diagnosis, there has been increasing the necessity of unstained microscopy capable of performing a microscopic observation without staining a sample by means of a fluorescent probe or the like. The requirements that this unstained microscopy should satisfy are mainly (1) and (2) below.
(1) High optical resolution (for example, lateral resolution<50 nm and axial resolution<100 nm).
(2) Discrimination capability of an observation object inside a sample.

As a new unstained microscopy that may satisfy these requirements, a stimulated emission microscopy was proposed (see WO 2011/099269, or the like).

SUMMARY

One aspect of a super-resolution observation device exemplifying the present embodiment includes an illumination optical system that focus a first illuminating light at optical frequency $\omega_1$ and a second illuminating light at optical frequency $\omega_2$ on a region of an observation object plane; a modulation unit that modulates a property of the first illuminating light heading toward the region at a modulation frequency $f_m$; and an extraction unit that extracts a component at the optical frequency $\omega_1$ or $\omega_2$ from a light generated in the region according to the first illuminating light and the second illuminating light, the component of which the property changes at a frequency higher than the modulation frequency $f_m$.

One aspect of the super-resolution observation device exemplifying the present embodiment includes an illumination optical system that focus an illuminating light at an optical frequency $\omega_1$ on a region of an observation object plane; a modulation unit that modulates a property of the illuminating light heading toward the region at a modulation frequency $f_m$; and an extraction unit that extracts a component at the optical frequency $\omega_1$ from a light generated in the region according to the illuminating light, the component of which the property changes at a frequency higher than the modulation frequency $f_m$.

One aspect of a super-resolution observation method exemplifying the present embodiment includes focusing a first illuminating light at optical frequency $\omega_1$ and a second illuminating light at optical frequency $\omega_2$ on a region of an observation object plane; modulating a property of the first illuminating light heading toward the region at a modulation frequency $f_m$; and extracting a component at the optical frequency $\omega_1$ or $\omega_2$ from a light generated in the region according to the first illuminating light and the second illuminating light, the component of which the property changes at a frequency higher than the modulation frequency $f_m$.

One aspect of the super-resolution observation method exemplifying the present embodiment includes focusing an illuminating light at optical frequency $\omega_1$ on a region of an observation object plane; modulating a property of the illuminating light heading toward the region at a modulation frequency $f_m$; and extracting a component at the optical frequency $\omega_1$ from a light generated in the region according to the illuminating light, the component of which the property changes at a frequency higher than the modulation frequency $f_m$.

BRIEF DESCRIPTION OF THE DRAWINGS

FIG. 3A and FIG. 3B are time-variable waveforms of the excitation light and the stimulation light to be incident on the observation object plane $P_0$ (where modulation of the excitation light is visualized).

FIG. 11 is a diagram comparing a light incident on respective regions of the light spot S and respective lights emitted from the respective regions in the fifth embodiment.

DETAILED DESCRIPTION OF THE EMBODIMENTS

A stimulated emission microscopy utilizes an energy level peculiar to an observation object, to thus be able to sufficiently satisfy the requirement (2) described in Description of the Related Art, but still has room for improvement for satisfying the requirement (1), and thus the current problems exist here.

Thus, the present invention provides a super-resolution observation device and a super-resolution observation method that are capable of performing a super-resolution observation on a sample without staining the sample so as to be able to solve the above-described problems.

Hereinafter, there will be explained embodiments.

First Embodiment

Hereinafter, there will be explained a super-resolution microscopy utilizing a stimulated emission process as a first embodiment of the present invention.

Figure 1:
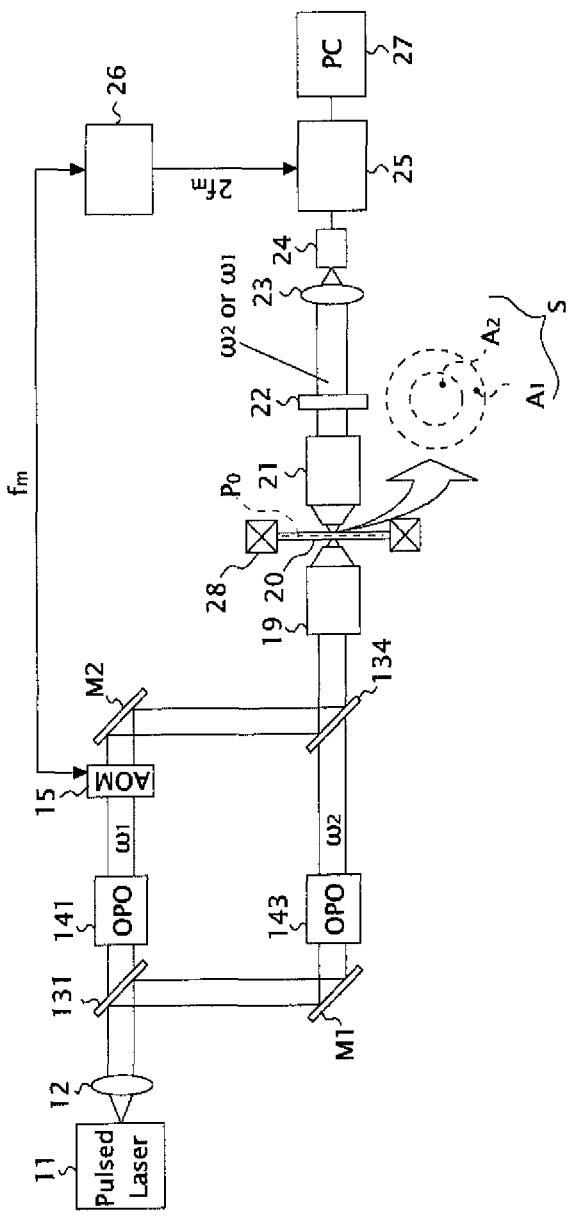
FIG. 1 is a configuration diagram of a super-resolution microscopy of a first embodiment.

FIG. 1 is a configuration diagram of the super-resolution microscopy of the first embodiment. As illustrated in FIG. 1, in the super-resolution microscopy, there are placed a pulsed laser light source 11, a lens 12, a beam splitter 131, a mirror M1, optical parametric oscillators (OPO: optical parametric oscillator) 141 and 143, an acousto-optics modulator (AOM: Acousto-optics modulator) 15, a mirror M2, a dichroic mirror 134, an objective lens 19, a sample 20, a sample stage 28, an objective lens 21, a wavelength selection filter 22, a collecting lens 23, a light detector 24 such as a photodiode, a lock-in amplifier 25, a signal generator 26, and a personal computer 27.

The pulsed laser light source 11 is a pulsed laser light source such as a femtosecond pulsed laser light source or picosecond pulsed laser light source. A repetition frequency $f_r$ of pulse oscillation performed by the pulsed laser light source 11 is, for example, 80 MHz, and a pulse width $\Delta T$ of a pulsed laser light that the pulsed laser light source 11 oscillates is, for example, several hundred fs (femtoseconds).

A pulsed laser light emitted from the pulsed laser light source 11 is turned into a collimated light flux having a large diameter by the lens 12 to be incident on the beam splitter 131. The pulsed laser light incident on the beam splitter 131 is split into a pulsed laser light that transmits through the beam splitter 131 and a pulsed laser light to be reflected by the beam splitter 131, and the pulsed laser light transmitted through the beam splitter 131 is incident on the optical parametric oscillator 141.

The pulsed laser light reflected by the beam splitter 131 is reflected by the mirror M1 to be incident on the optical parametric oscillator 143.

The optical parametric oscillator 141 converts an optical frequency of the incident pulsed laser light into $\omega_1$, and the optical parametric oscillator 143 converts an optical frequency of the incident pulsed laser light into $\omega_2$. Here, a magnitude relation between the optical frequencies $\omega_1$ and $\omega_2$ is set to $\omega_1 > \omega_2$.

The acousto-optics modulator 15 is placed in an emission optical path of the optical parametric oscillator 141, namely in an independent optical path of the pulsed laser light at the optical frequency $\omega_1$, and modulates an intensity of the pulsed laser light with a sine wave of a single frequency $f_m$ over a time direction. Note that a modulation waveform (the modulation frequency $f_m$) of the pulsed laser light by means of the acousto-optics modulator 15 is controlled by a control signal given by the signal generator 26.

The pulsed laser light at the optical frequency $\omega_1$ emitted from the optical parametric oscillator 141 is reflected by the mirror M2 via the acousto-optics modulator 15, and is reflected by the dichroic mirror 134.

The pulsed laser light at the optical frequency $\omega_2$ emitted from the optical parametric oscillator 143 transmits through the dichroic mirror 134, and an optical path of the pulsed laser light at the optical frequency $\omega_2$ and the optical path of the pulsed laser light at the optical frequency $\omega_1$ are coaxially combined.

The pulsed laser lights at the optical frequencies $\omega_1$ and $\omega_2$ with a mutually combined optical path are focused on a minute region of an observation object plane $P_0$ of the sample 20 by the objective lens 19 to form light spots.

Note that between the light spot that the pulsed laser light at the optical frequency $\omega_1$ forms on the observation object plane $P_0$ and the light spot that the pulsed laser light at the optical frequency $\omega_2$ forms on the observation object plane $P_0$, a shape, a position, and a size are substantially common. Hereinafter, the light spot that the pulsed laser light at the optical frequency $\omega_1$ forms on the observation object plane $P_0$ and the light spot that the pulsed laser light at the optical frequency $\omega_2$ forms on the observation object plane $P_0$ will be just referred to as a "light spot S" with no distinction.

Here, a relation between an optical path length of the pulsed laser light at the optical frequency $\omega_1$ and an optical path length of the pulsed laser light at the optical frequency $\omega_2$ is adjusted beforehand so that the order in which they are irradiated to the observation object plane $P_0$ becomes an order below.

(1) The pulsed laser light at the optical frequency $\omega_1$
(2) The pulsed laser light at the optical frequency $\omega_2$ Between the above, the pulsed laser light at the optical frequency $\omega_1$ irradiating first has a function of shifting an energy level of electrons of a specific observation object substance existing in the light spot S to an excitation level (light absorption), and the pulsed laser light at the optical frequency $\omega_2$ irradiating next has a function of shifting the excited electrons to a ground state (stimulated emission) to generate a stimulated emission light at the optical frequency $\omega_2$.

Thus, the pulsed laser light at the optical frequency $\omega_1$ irradiating first will be referred to as an "excitation light" and the pulsed laser light at the optical frequency $\omega_2$ irradiating next will be referred to as a "stimulation light" below.

Note that in the super-resolution microscopy of this embodiment, a combination of pulse shapes (pulsed light intensities and pulse widths) of the respective excitation light and stimulation light and the optical frequencies $\omega_1$ and $\omega_2$ is adjusted beforehand so as to cause the above-described stimulated emission process (above-described excitation and stimulated emission) to occur in the observation object substance existing in the light spot S. The optical frequencies $\omega_1$ and $\omega_2$ are each desirably set to be within a range of from ultraviolet region to near-infrared region wavelengths approximately in terms of a wavelength, and the pulse width is desirably set to a time width of from a picosecond to a femtosecond.

Further, in the super-resolution microscopy of this embodiment, the pulsed light intensities of the excitation light and the stimulation light are each adjusted to an appropriate value beforehand so as to cause a light absorption amount in a central region $A_2$ of the light spot S to be saturated and prevent a light absorption amount in a peripheral region $A_1$ of the light spot S from being saturated. Incidentally, in order to judge whether or not the light absorption amount is saturated, it is only necessary to judge whether or not a later-described high-frequency component is detected.

Note that the pulse shapes (pulsed light intensities and pulse widths) of the respective excitation light and stimulation light can be adjusted by a shape of pulse oscillated by the pulsed laser light source 11 and transmittance and reflectance of the beam splitter 131. Alternatively, it is also possible to dispose an ND filter (not illustrated) in at least one of the optical paths of the excitation light and the stimulation light and adjust a transmittance of the ND filter.

Figure 2A:
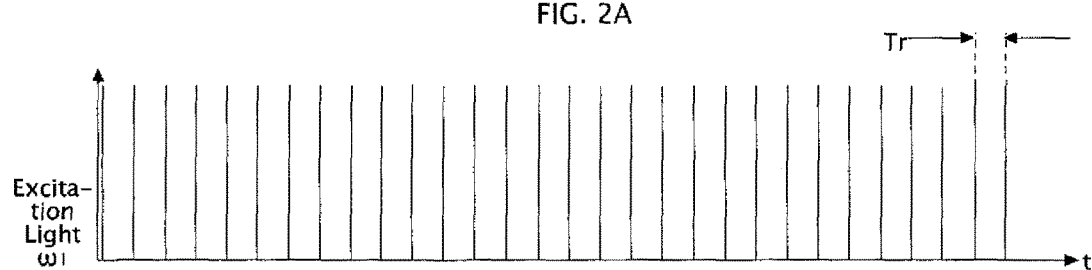
FIG. 2A to FIG. 2C are time-variable waveforms of an excitation light and a stimulation light to be incident on an observation object plane $P_0$ (where modulation of the excitation light is not visualized).
Figure 2B:
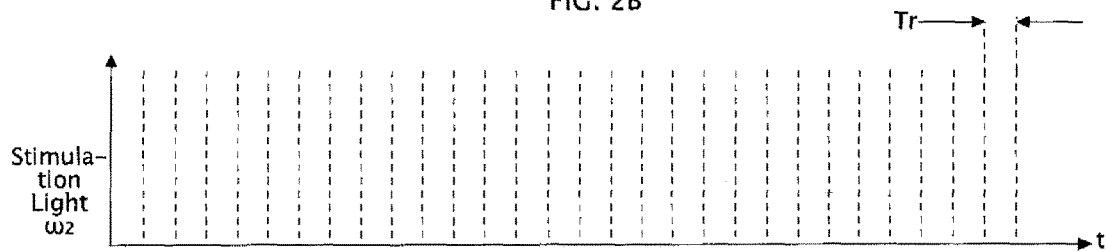

FIG. 2A illustrates a time-variable waveform of the excitation light to be incident on the observation object plane $P_0$, and FIG. 2B illustrates a time-variable waveform of the stimulation light to be incident on the observation object plane $P_0$.

Figure 2C:
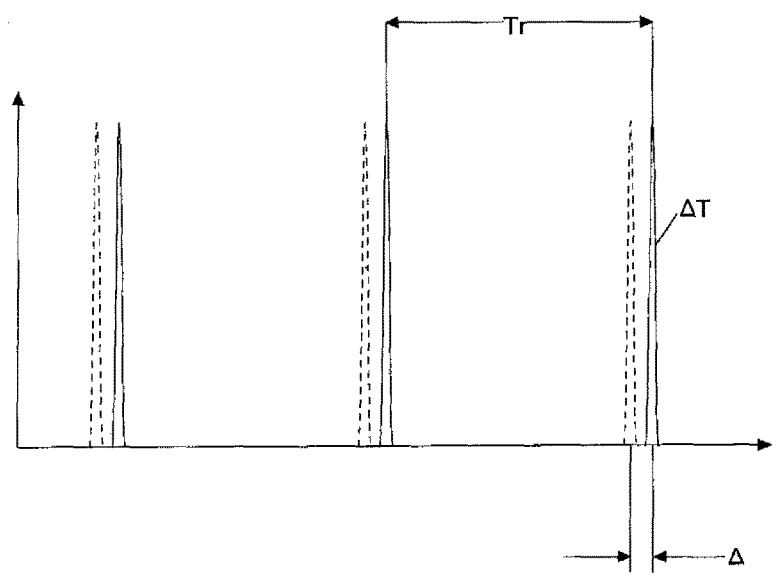

As illustrated in FIG. 2A and FIG. 2B, a repetitive pitch Tr of a pulse is common between the excitation light and the stimulation light, but a timing at which a pulse reaches the observation object plane $P_0$ differs by a slight amount between the excitation light and the stimulation light, FIG. 2C is one where waveforms of three pulses of each of the excitation light and the stimulation light are illustrated on the same coordinates in an enlarged manner. In FIG. 2C, one indicated by a solid line is a pulse of the excitation light, and one indicated by a dotted line is a pulse of the stimulation light. As illustrated in FIG. 2C, a difference Δ between the timing of the pulse of the excitation light reaching the observation object plane $P_0$ and the timing of the pulse of the stimulation light reaching the observation object plane $P_0$ is an extent slightly larger than a pulse width ΔT of each of the excitation light and the stimulation light, for example, several hundred fs (femtoseconds).

Note that in order to adjust the difference Δ between the timings of the excitation light and the stimulation light reaching the observation object plane $P_0$, an optical path length adjusting mechanism made of a movable mirror and the like (not illustrated) is desirably provided in at least one optical path of the independent optical path of the excitation light and the independent optical path of the stimulation light in the super-resolution microscopy of this embodiment.

Further, although in FIG. 2A and FIG. 2B, modulation of the excitation light performed by the acousto-optics modulator 15 is not visualized, visualization of the modulation is as illustrated in FIG. 3A and FIG. 3B. As illustrated in FIG. 3A, the modulation frequency $f_m$ of the excitation light by means of the acousto-optics modulator 15 is sufficiently low as compared to the repetition frequency $f_r$ of a pulse and satisfies at least a relation of $f_m \leq f_r/2$, where, for example, $f_m$ is several MHz or so. Note that in FIG. 3A, a symbol $T_m$ denotes a modulation pitch of the excitation light (=a reciprocal of the modulation frequency $f_m$).

Then, returning to FIG. 1, the sample 20 is, for example a transparent living cell contained in an incubation container together with a culture fluid, and a specific substance in this living cell (for example, a specific protein such as hemoglobin) is the observation object substance. The above-described stimulated emission process utilizes displacement of an energy level peculiar to the observation object substance (light absorption), so that the observation object substance does not have to be fluorescently stained beforehand.

The sample stage 28 is a transmission-type stage that supports the sample 20, moves the sample 20 over an optical axis direction (Z direction), and at the same time, moves the sample 20 over a direction perpendicular to an optical axis (XY direction). When the sample stage 28 moves the sample 20 over the Z direction, a depth of the observation object plane $P_0$ inside the sample 20 is adjusted, and when the sample stage 28 moves the sample 20 over the XY direction, the observation object plane $P_0$ can be two-dimensionally scanned in the light spot S.

Lights emitted from the light spot S of the observation object plane $P_0$, namely the excitation light emitted from the light spot S (additional excitation light), the stimulation light emitted from the light spot (additional stimulation light), and the stimulated emission light generated in the light spot are incident on the objective lens 21 from a tip side of the objective lens 21.

Specifications (a numerical aperture, a magnification, and the like) of the objective lens 21 are the same as those of the objective lens 19, and a locational relationship and an attitude relationship between the objective lens 21 and the objective lens 19 are symmetrical with respect to the observation object plane $P_0$. Note that the specifications of the objective lens 21 and the specifications of the objective lens 19 are made common here, but it is acceptable that they are not common completely. For example, a numerical aperture of the objective lens 21 may be larger than a numerical aperture of the objective lens 19.

The lights incident on the objective lens 21 from the tip side, namely the excitation light emitted from the light spot S of the observation object plane $P_0$ (additional excitation light), the stimulation light emitted from the light spot S of the observation object plane $P_0$ (additional stimulation light), and the stimulated emission light emitted from the light spot S of the observation object plane $P_0$ emits from a pupil side of the objective lens 21 to then head toward the light detector 24 via the wavelength selection filter 22 and the collecting lens 23 in order.

Here, the wavelength selection filter 22 includes wavelength-selectivity characteristics that cause the wavelength selection filter 22 to block one of a light at the optical frequency $\omega_1$ and a light at the optical frequency $\omega_2$ and allow the other of them to pass therethrough provided thereto. Hereinafter, it is assumed that the wavelength selection filter 22 allows a light at the optical frequency $_1$ to pass therethrough and blocks a light at the optical frequency $\omega_2$.

Therefore, the additional excitation light (optical frequency $\omega_1$) emitted from the light spot S is incident on the light detector 24, and the additional stimulation light and the stimulated emission light (optical frequency $\omega_2$) emitted from the light spot S are not incident on the light detector 24.

The light detector 24 is a photoelectric conversion element that converts an intensity of incident light into an electrical signal, such as a photodiode.

The lock-in amplifier 25 detects, from an electrical signal output from the light detector 24, a component to change at a frequency ($2f_m$) double the modulation frequency $f_m$ of the excitation light as a signal. Note that a detection frequency and a detection timing of the lock-in amplifier 25 are controlled by a control signal given by the signal generator 26.

The personal computer 27 takes in the signal detected by the lock-in amplifier 25. Further, the personal computer 27, during the aforementioned scanning, performs taking-in of a signal when the light spot S is located at each position of the observation object plane $P_0$ (specifically, when the central region $A_2$ of the light spot S is located at each position of the observation object plane $P_0$), and creates a distribution of signals on the observation object plane $P_0$ as a super-resolution image, and then displays it on a not-illustrated monitor.

Hereinafter, there will be explained a super-resolution effect of the super-resolution microscopy with reference to FIG. 4.

Figure 4:
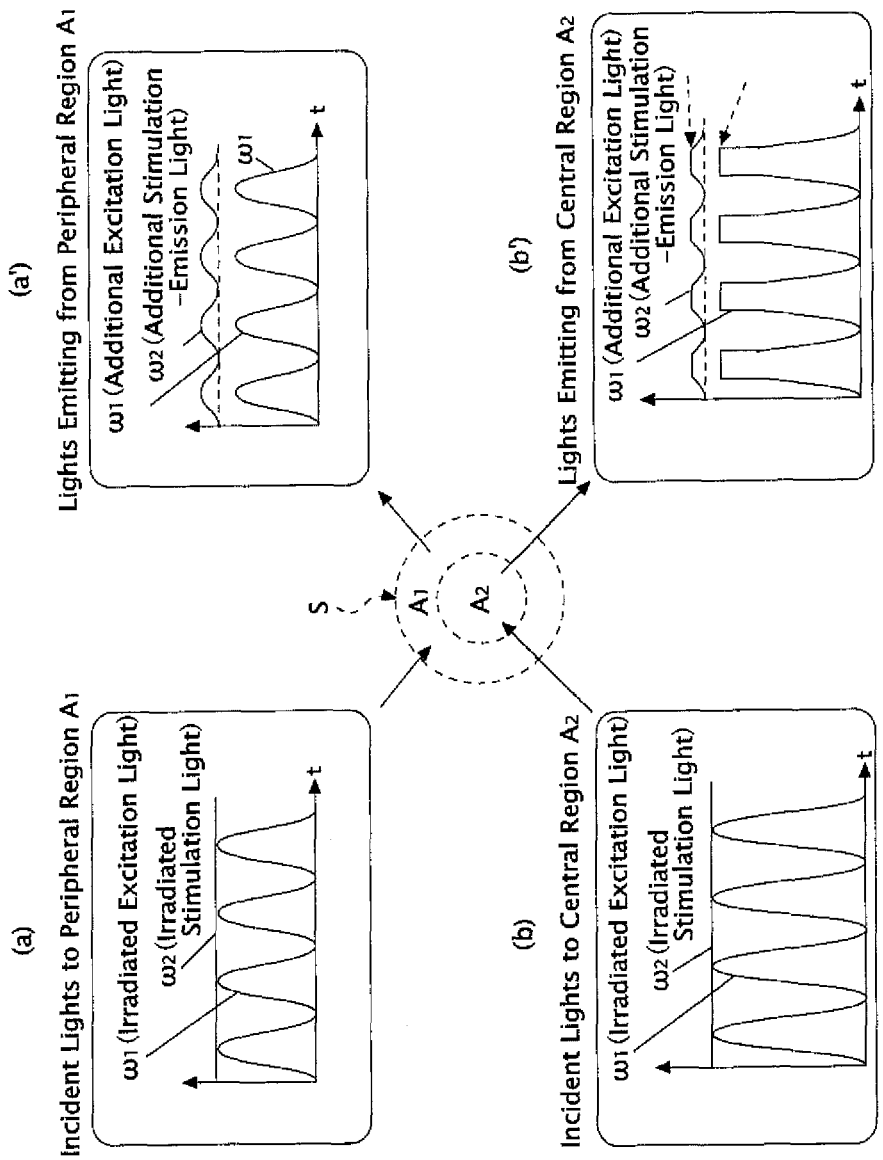
FIG. 4 is a diagram comparing respective lights incident on respective regions of a light spot S and respective lights emitted from the respective regions.

The part (a) of FIG. 4 illustrates time-variable waveforms of lights irradiating to the peripheral region $A_1$ of the light spot S, a symbol $\omega_1$ in the part (a) of FIG. 4 denotes a waveform of the excitation light (irradiated excitation light), and a symbol $\omega_2$ in the part (a) of FIG. 4 denotes a waveform of the stimulation light (irradiated stimulation light) (note that in FIG. 4, illustration of small pulses is omitted and only an envelope of pulses is illustrated).

The part (a') of FIG. 4 illustrates time-variable waveforms of lights emitting from the peripheral region $A_1$ of the light spot S, a symbol $\omega_1$ in the part (a') of FIG. 4 denotes a waveform of the additional excitation light that does not contribute to light absorption, and a symbol $\omega_2$ in the part (a') of FIG. 4 denotes a combined waveform of the stimulation light and the stimulated emission light (to be referred to as an "additional guide-emission light" in a summarized manner, hereinafter).

The part (b) of FIG. 4 illustrates time-variable waveforms of lights irradiating to the central region $A_2$ of the light spot S, a symbol $\omega_1$ in the part (b) of FIG. 4 denotes a waveform of the excitation light (irradiated excitation light), and a symbol $\omega_2$ in the part (b) of FIG. 4 denotes a waveform of the stimulation light (irradiated stimulation light).

The part (b) of FIG. 4 illustrates time-variable waveforms of lights emitting from the central region $A_2$ of the light spot S, a symbol $\omega_1$ in the part (b') of FIG. 4 denotes a waveform of the additional excitation light that does not contribute to light absorption, and a symbol $\omega_2$ in the part (b') of FIG. 4 denotes a combined waveform of the stimulation light and the stimulated emission light (to be referred to as an "additional guide-emission light" in a summarized manner, hereinafter).

Then, in the super-resolution microscopy of this embodiment, as described above, the excitation light is modulated by means of the modulation frequency $f_m$, so that an intensity of the excitation light irradiated to the peripheral region $A_1$ (symbol $\omega_1$ in the part (a) of FIG. 4) and an intensity of the excitation light irradiated to the central region $A_2$ (symbol $\omega_1$ in the part (b) of FIG. 4) both time-vary by means of the modulation frequency $f_m$.

Further, in the super-resolution microscopy of this embodiment, these irradiated excitation lights time-vary by means of the modulation frequency $f_m$, so that a light absorption amount in the peripheral region $A_1$ (not illustrated) and a light absorption amount in the central region $A_2$ (not illustrated) also time-vary by means of the frequency $f_m$ basically.

Therefore, in the super-resolution microscopy of this embodiment, a frequency component at the frequency $f_m$ is generated in each of the time-variable waveform of the additional excitation light emitting from the peripheral region $A_1$ (symbol $\omega_1$ in the part (a') of FIG. 4) and the time-variable waveform of the additional excitation light emitting from the central region $A_2$ (symbol $\omega_1$ in the part (b') of FIG. 4).

However, in the super-resolution microscopy microscopy of this embodiment, the light absorption amount in the peripheral region $A_1$ (not illustrated) is not saturated, but the light absorption amount in the central region $A_2$ (not illustrated) is saturated.

Accordingly, a high-frequency component over the frequency $f_m$ is not generated in the time-variable waveform of the additional excitation light emitting from the peripheral region $A_1$ (symbol $\omega_1$ in the part (a') of FIG. 4), whereas a high-frequency component over the frequency $f_m$ (component at the frequency $2f_m$, for example) is generated in the time-variable waveform of the additional excitation light emitting from the central region $A_2$ (symbol $\omega_1$ in the part (b') of FIG. 4) (see a dotted line arrow in the part (b') of FIG. 4).

Then, the lock-in amplifier 25 of this embodiment lock-in detects only a signal to change at the frequency $2f_m$ from the electrical signal output from the light detector 24 (=a light intensity signal at the optical frequency $\omega_1$).

In this signal (=light intensity signal at the optical frequency $\omega_1$ to change at the frequency $2f_m$), the light absorption amount in the peripheral region $A_1$ is not reflected, but the light absorption amount in the central region $A_2$ is reflected.

Accordingly, the lock-in amplifier 25 of this embodiment can extract only the high-frequency component of the additional excitation light emitted from the central region $A_2$ (symbol $\omega_1$ in the part (b') of FIG. 4) (component to change at the frequency $2f_m$) from the lights generated in the light spot S.

Accordingly, the super-resolution microscopy of this embodiment can limit an obtaining origin of a signal only to the central region $A_2$ smaller than the light spot S, namely perform a super-resolution observation on a density distribution of the observation object substance in the sample 20.

Modified Example of First Embodiment

Note that in this embodiment, the detection frequency of lock-in detection performed by the lock-in amplifier 25 is set to the double ($2f_m$) of the modulation frequency $f_m$ of the excitation light, but may be set to another value larger than the modulation frequency $f_m$. For example, the detection frequency may be set to $N \times f_m$, (where N is an integer of 2 or more). By increasing the detection frequency as above, the super-resolution effect can be further increased. This is because a region that can be a generation origin of the high-frequency component out of the light spot S is limited only to a region with a particularly high light intensity, namely only to an extremely narrow region. Therefore, the higher the detection frequency is, the more the super-resolution effect increases.

Further, although in this embodiment, the optical frequency of a light that should be incident on the light detector 24 is set the same as the optical frequency $\omega_1$ of the excitation light, it may be set the same as the optical frequency $\omega_2$ of the stimulation light. In the case, the wavelength selection filter 22 includes wavelength-selectivity characteristics that cause the wavelength selection filter 22 to block a light at the optical frequency $\omega_1$ and allow a light at the optical frequency $\omega_2$ to pass therethrough provided thereto.

In this case, the lock-in amplifier 25 can extract a high-frequency component of the additional guide-emission light (symbol $\omega_2$ in the part (b') of FIG. 4) in place of the high-frequency component of the additional excitation light (symbol $\omega_1$ in the part (b') of FIG. 4). The super-resolution observation is enabled also in this case. The reason is as follows.

That is, in each of the time-variable waveform of the additional guide-emission light emitting from the peripheral region $A_1$ (symbol $\omega_2$ in the part (a') of FIG. 4) and the time-variable waveform of the additional guide-emission light emitting from the central region $A_2$ (symbol $\omega_2$ in the part (b') of FIG. 4), a frequency component at the frequency $f_m$ is generated.

However, the light absorption amount in the peripheral region $A_1$ (not illustrated) is not saturated, but the light absorption amount in the central region $A_2$ (not illustrated) is saturated. In this case, a stimulated emission amount in the peripheral region $A_1$ (not illustrated) is not saturated, but a stimulated emission amount in the central region $A_2$ (not illustrated) is saturated.

Therefore, a high-frequency component over the frequency $f_m$ is not generated in the time-variable waveform of the additional guide-emission light emitting from the peripheral region $A_1$ (symbol $\omega_2$ in the part (a') of FIG. 4), whereas a high-frequency component over the frequency $f_m$ (for example, component at the frequency $2f_m$) is generated in the time-variable waveform of the additional guide-emission light emitting from the central region $A_2$ (symbol $\omega_2$ in the part (b') of FIG. 4) (see a dotted line arrow in the part (b') of FIG. 4).

Note that the super-resolution microscopy of this embodiment may be configured so as to be capable of switching the wavelength selection filter 22 between two wavelength selection filters. One of the two wavelength selection filters includes wavelength-selectivity characteristics that cause the wavelength selection filter to block a light at the optical frequency $\omega_2$ and allow a light at the optical frequency $\omega_1$ to pass therethrough provided thereto, and the other of the two wavelength selection filters includes wavelength-selectivity characteristics that cause the wavelength selection filter to block a light at the optical frequency $\omega_1$ and allow a light at the optical frequency $\omega_2$ to pass therethrough provided thereto.

Further, although in the super-resolution microscopy of this embodiment, a time difference is provided between the timing of the excitation light reaching the sample 20 and the timing of the stimulation light reaching the sample 20, this time difference may be set to be zero. However, in the case, a wavelength difference of 3600 cm$^{-1}$ or more in terms of energy is desirably provided between the excitation light and the stimulation light.

Second Embodiment

Hereinafter, there will be explained a super-resolution microscopy utilizing an excited-state absorption (ESA: Excited-State Absorption) process as a second embodiment of the present invention. Here, only differences from the first embodiment are explained.

First, in this embodiment, the pulsed laser light at the optical frequency $\omega_1$ is used as an excitation light and the pulsed laser light at the optical frequency $\omega_2$ is used as an ESA light. The optical frequency $\omega_1$ is desirably set to be within a range of from ultraviolet region to visible region wavelengths approximately in terms of a wavelength, and the optical frequency $\omega_2$ is desirably set to be within a range of from visible region to near-infrared region wavelengths approximately in terms of a wavelength.

Further, in this embodiment, a combination of pulse shapes (pulsed light intensities and pulse widths) of the respective excitation light and ESA light and the optical frequencies $\omega_1$ and $\omega_2$ is set so as to cause the ESA process to occur in the observation object substance existing in the light spot S.

The ESA process is a process of first shifting an energy level of electrons of a specific observation object substance to an excitation level by means of the excitation light (light absorption) and then shifting the excited electrons to a higher level by means of the ESA light.

Further, in this embodiment, the pulsed light intensities of the excitation light and the ESA light are set to appropriate values so as to cause the light absorption amount in the central region $A_2$ of the light spot S to be saturated and prevent the light absorption amount in the peripheral region $A_1$ of the light spot S from being saturated.

Figure 5:
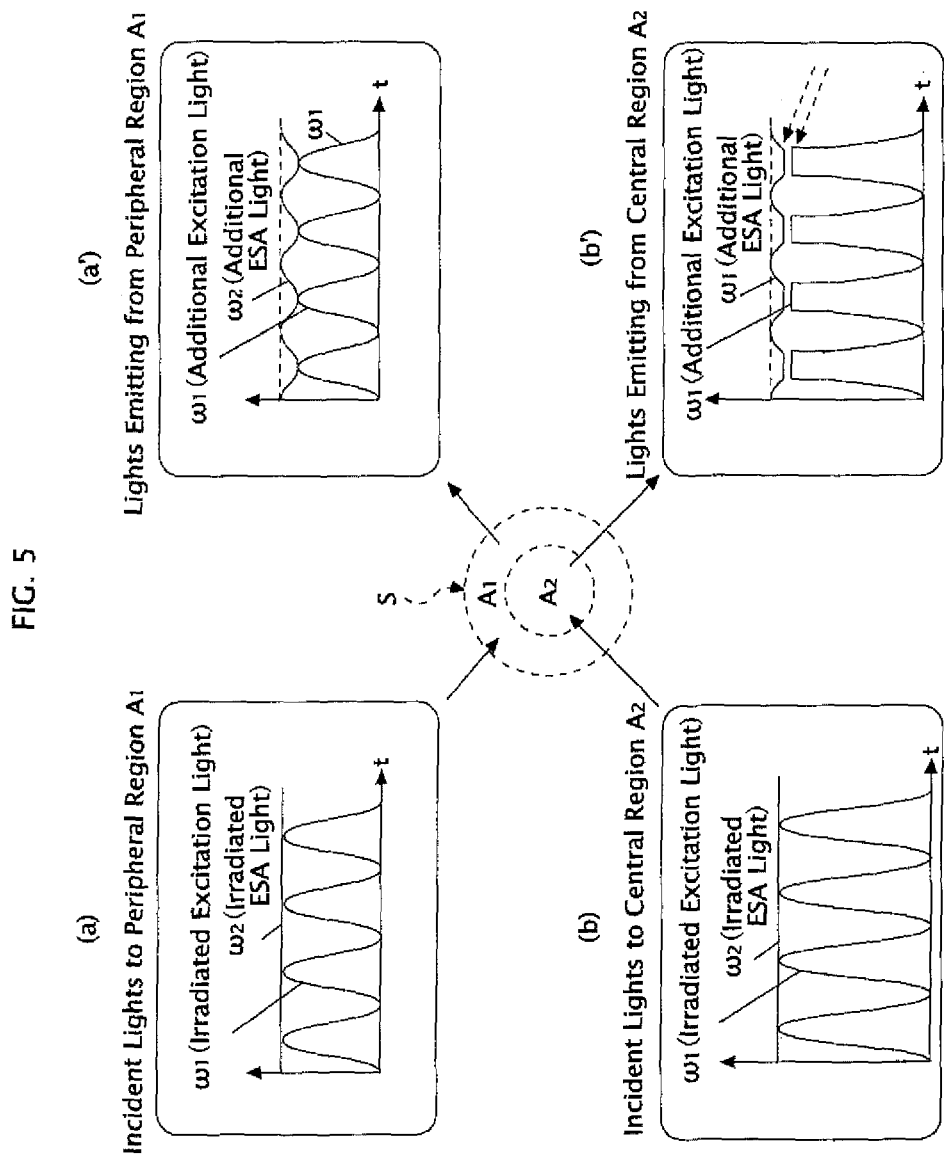
FIG. 5 is a diagram comparing respective lights incident on respective regions of the light spot S and respective lights emitted from the respective regions in a second embodiment.

FIG. 5 illustrates time-variable waveforms of respective lights in this embodiment. Main difference from the time-variable waveforms in the first embodiment (FIG. 4) is, as illustrated in FIG. 5, that a phase of the time-variable waveform of a light at the optical frequency $\omega_2$ emitting from the light spot S (=additional ESA light that does not contribute to the ESA process) is displaced by $\pi$. This is because as an intensity of the excitation light is higher, an intensity of the additional ESA light decreases in the ESA process.

However, in this embodiment as well, a high-frequency component over the frequency $f_m$ is not generated in each of the additional excitation light and the additional ESA light emitting from the peripheral region $A_1$ as illustrated in the part (a') of FIG. 5, whereas a high-frequency component over the frequency $f_m$ is generated in each of the additional excitation light and the additional ESA light emitted from the central region $A_2$ as illustrated in the part (b') of FIG. 5.

Accordingly, in a signal to be detected by the lock-in amplifier 25 in this embodiment, the light absorption amount in the peripheral region $A_1$ is not reflected, but the light absorption amount in the central region $A_2$ is reflected.

Accordingly, in this embodiment as well, a super-resolution observation of the sample 20 is enabled similarly to the first embodiment.

Modified Example of Second Embodiment

Note that in this embodiment, the detection frequency of lock-in detection performed by the lock-in amplifier 25 is set to the double ($2f_m$) of the modulation frequency $f_m$, but it may be set to another value larger than the modulation frequency $f_m$. For example, the detection frequency may be set to N×$f_m$, (where N is an integer of 2 or more). By increasing the detection frequency as above, the super-resolution effect can be further increased. This is because a region that can be a generation origin of the high-frequency component out of the light spot S is limited only to a region with a particularly high light intensity, namely only to an extremely narrow region. Thereby, the higher the detection frequency is, the more the super-resolution effect increases.

Further, although in this embodiment, the optical frequency of a light that should be incident on the light detector 24 is set the same as the optical frequency $\omega_1$ of the excitation light, it may be set the same as the optical frequency $\omega_2$ of the ESA light. In the case, the wavelength selection filter 22 includes wavelength-selectivity characteristics that cause the wavelength selection filter 22 to block a light at the optical frequency $\omega_1$ and allow a light at the optical frequency $\omega_2$ to pass therethrough provided thereto.

Further, the super-resolution microscopy of this embodiment may be configured so as to be capable of switching the wavelength selection filter 22 between two wavelength selection filters. One of the two wavelength selection filters includes wavelength-selectivity characteristics that cause the wavelength selection filter to block a light at the optical frequency $\omega_2$ and allow a light at the optical frequency $\omega_1$ to pass therethrough provided thereto, and the other of the two wavelength selection filters includes wavelength-selectivity characteristics that cause the wavelength selection filter to block a light at the optical frequency $\omega_1$ and allow a light at the optical frequency $\omega_2$ to pass therethrough provided thereto.

Third Embodiment

Hereinafter, there will be explained a super-resolution microscopy utilizing a ground state depletion (GSD: Ground State Depletion) process as a third embodiment of the present invention. Here, only differences from the first embodiment are explained.

Figure 6:
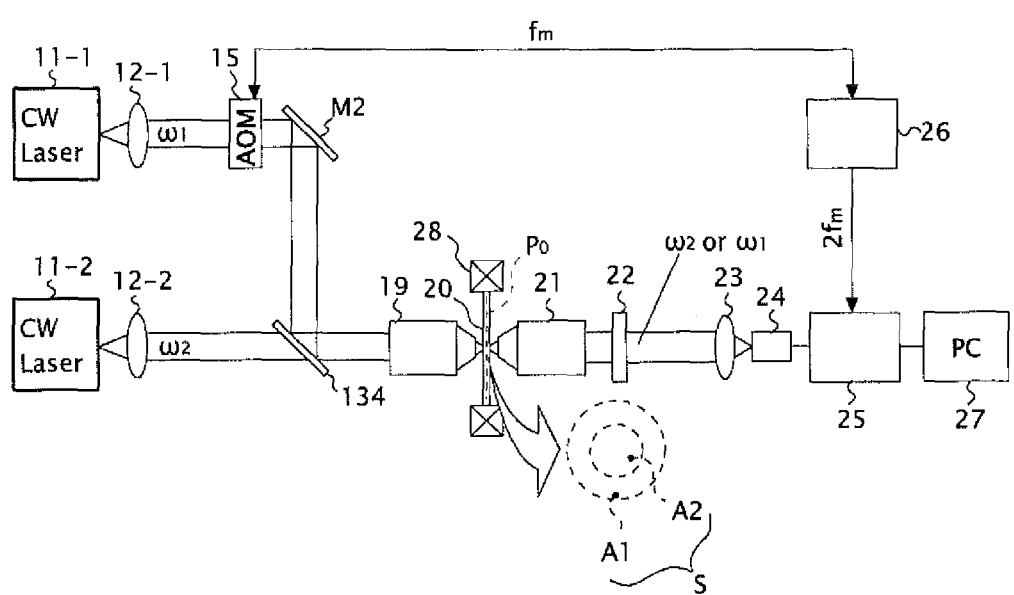
FIG. 6 is a configuration diagram of a super-resolution microscopy of a third embodiment.

FIG. 6 is a configuration diagram of the super-resolution microscopy of this embodiment. As illustrated in FIG. 6, the super-resolution microscopy of this embodiment is that in place of the pulsed laser light source 11 and the lens 12 in the super-resolution microscopy of the first embodiment, CW laser light sources 11-1 and 11-2 and lenses 12-1 and 12-2 are used (CW: Continuous Wave) and the optical parametric oscillators 141 and 143, the beam splitter 131, and the mirror M1 are omitted. The CW laser light source 11-1 emits a CW laser light at the optical frequency $\omega_1$ via the lens 12-1, and the CW laser light source 11-2 emits a CW laser light at the optical frequency $\omega_2$ via the lens 12-2.

In this embodiment, between them, the CW laser light at the optical frequency $\omega_1$ is used as a first excitation light, and the CW laser light at the optical frequency $\omega_2$ is used as a second excitation light.

Further, in this embodiment, a combination of intensities of the first excitation light and the second excitation light and the optical frequencies $\omega_1$ and $\omega_2$ is set so as to cause the GSD process to occur in the observation object substance existing in the light spot S. However, in this embodiment, a magnitude relation between the optical frequencies $\omega_1$ and $\omega_2$ is $\omega_1 < \omega_2$. Specifically, a value relation between the optical frequencies $\omega_1$ and $\omega_2$ is set to a value relation such that excitation from a ground state to an excited state in the GSD process occurs. Further, the optical frequencies $\omega_1$ and $\omega_2$ are each desirably set to be within a range of from ultraviolet region to visible region wavelengths approximately in terms of a wavelength.

The GSD process is a process of shifting an energy level of electrons of a specific observation object substance to a first excitation level by means of the first excitation light (light absorption) and shifting the remaining electrons of the same kind of the observation object substance to the first excitation level by means of the second excitation light.

Further, in this embodiment, the intensities of the first excitation light and the second excitation light are set to appropriate values so as to cause the light absorption amount in the central region $A_2$ of the light spot S to be saturated and prevent the light absorption amount in the peripheral region $A_1$ of the light spot S from being saturated.

Figure 7:
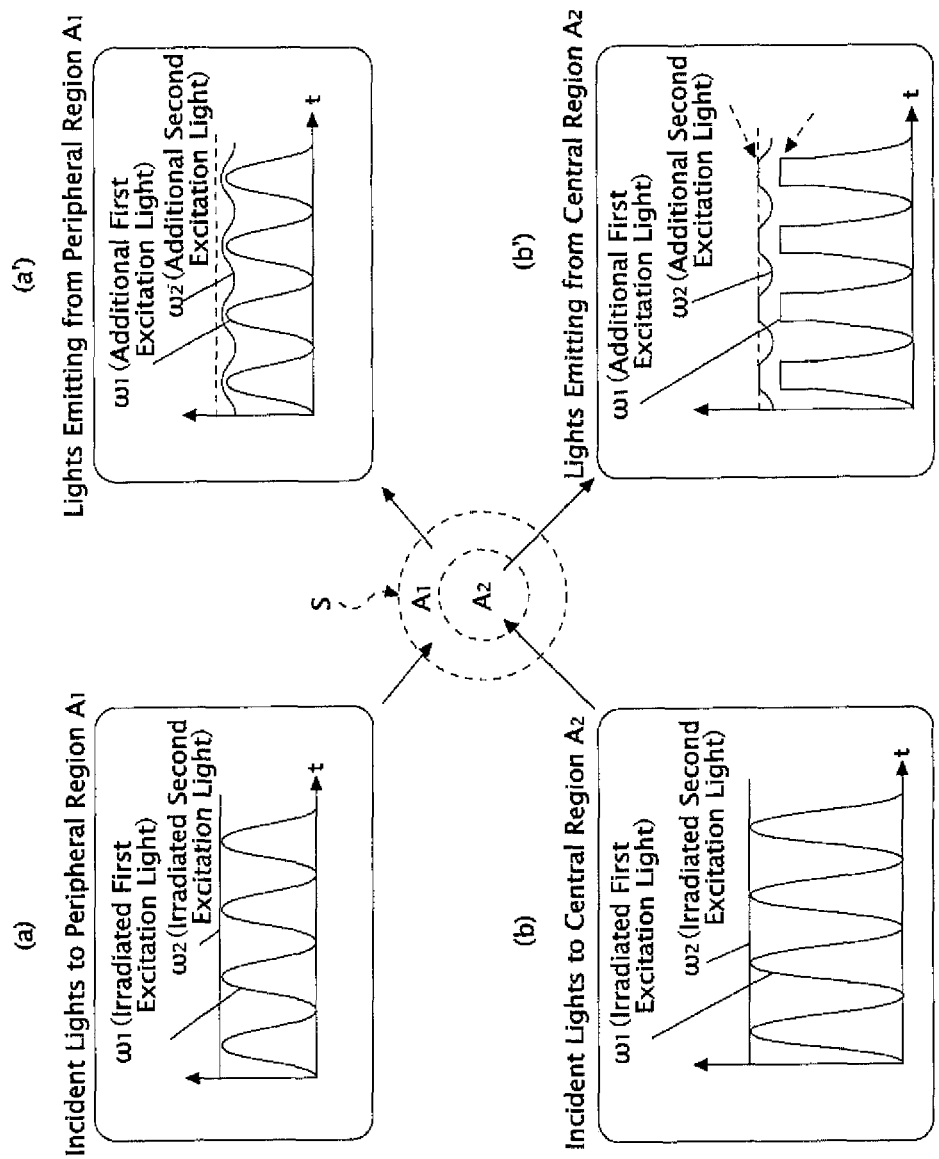
FIG. 7 is a diagram comparing respective lights incident on respective regions of the light spot S and respective lights emitted from the respective regions in the third embodiment.

FIG. 7 illustrates time-variable waveforms of respective lights in this embodiment. In this embodiment as well, a high-frequency component over the frequency $f_m$ is not generated in each of the additional first excitation light and the additional second excitation light emitting from the peripheral region $A_1$ as illustrated in the part (a') of FIG. 7, whereas a high-frequency component over the frequency $f_m$ is generated in each of the additional first excitation light and the additional second excitation light emitting from the central region $A_2$ as illustrated in the part (b') of FIG. 7.

Accordingly, in a signal to be detected by the lock-in amplifier 25 in this embodiment, the light absorption amount in the peripheral region $A_1$ is not reflected, but the light absorption amount in the central region $A_2$ is reflected.

Accordingly, in this embodiment as well, a super-resolution observation of the sample 20 is enabled similarly to the first embodiment.

Modified Example of Third Embodiment

Note that in this embodiment, the detection frequency of lock-in detection performed by the lock-in amplifier 25 is set to the double ($2f_m$) of the modulation frequency $f_m$, but it may be set to another value larger than the modulation frequency $f_m$. For example, the detection frequency may be set to $N \times f_m$, (where N is an integer of 2 or more). By increasing the detection frequency as above, the super-resolution effect can be further increased. This is because a region that can be a generation origin of the high-frequency component out of the light spot s is limited only to a region with a particularly high light intensity, namely only to an extremely narrow region. Thereby, the higher the detection frequency is, the more the super-resolution effect increases.

Further, although in this embodiment, the optical frequency of a light that should be incident on the light detector 24 is set the same as the optical frequency $\omega_1$ of the first excitation light, it may be set the same as the optical frequency $\omega_2$ of the second excitation light. In the case, the wavelength selection filter 22 includes wavelength-selectivity characteristics that cause the wavelength selection filter 22 to block a light at the optical frequency $\omega_1$ and allow a light at the optical frequency $\omega_2$ to pass therethrough provided thereto.

Further, the super-resolution microscopy of this embodiment may be configured so as to be capable of switching the wavelength selection filter 22 between two wavelength selection filters. One of the two wavelength selection filters includes wavelength-selectivity characteristics that cause the wavelength selection filter to block a light at the optical frequency $\omega_2$ and allow a light at the optical frequency $\omega_1$ to pass therethrough provided thereto, and the other of the two wavelength selection filters includes wavelength-selectivity characteristics that cause the wavelength selection filter to block a light at the optical frequency $\omega_1$ and allow a light at the optical frequency $\omega_2$ to pass therethrough provided thereto.

Further, although in the super-resolution microscopy of this embodiment, the CW laser light is used as each of the first excitation light and the second excitation light, a pulsed laser light may be used. A device configuration of the case of using the pulsed laser light is as explained in the first embodiment (see FIG. 1).

Fourth Embodiment

Hereinafter, there will be explained a super-resolution microscopy utilizing a one-photon absorption process as a fourth embodiment of the present invention. Here, only differences from the first embodiment are explained.

Figure 8:
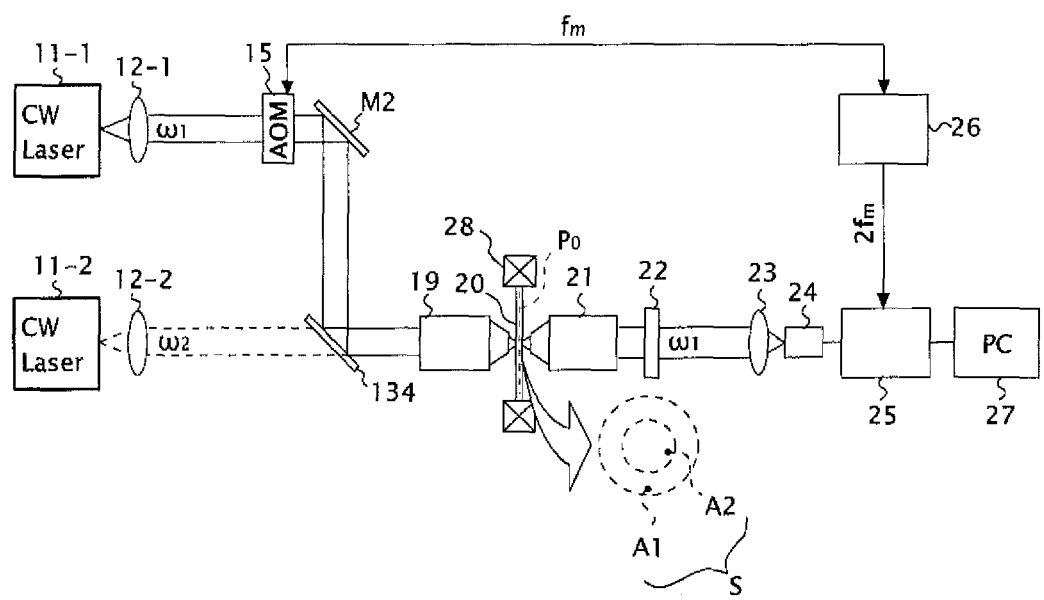
FIG. 8 is a configuration diagram of a super-resolution microscopy of a fourth embodiment.

FIG. 8 is a configuration diagram of the super-resolution microscopy of this embodiment. As illustrated in FIG. 8, the super-resolution microscopy of this embodiment is that in place of the pulsed laser light source 11 and the lens 12 in the super-resolution microscopy of the first embodiment, the CW laser light sources 11-1 and 11-2 and the lenses 12-1 and 12-2 are used (CW: Continuous Wave) and the optical parametric oscillators 141 and 143, the beam splitter 131, and the mirror M1 are omitted. The CW laser light source 11-1 emits the CW laser light at the optical frequency $\omega_1$ via the lens 12-1, and the CW laser light source 11-2 emits the CW laser light at the optical frequency $\omega_2$ via the lens 12-2.

However, in this embodiment, only the CW laser light at the optical frequency $\omega_1$ is used as the excitation light, and thus the CW laser light at the optical frequency $\omega_2$ heading toward the observation object plane $P_0$ is turned off. The CW laser light source 11-2 only needs to be turned off in order to turn off the CW laser light at the optical frequency $\omega_2$.

Further, in this embodiment, a combination of an intensity of the excitation light and the optical frequency $\omega_1$ is set so as to cause the one-photon absorption process to occur in the observation object substance existing in the light spot S. The optical frequency $\omega_1$ is desirably set to be within a range of from ultraviolet region to visible region wavelengths approximately in terms of a wavelength.

The one-photon absorption process is a process of shifting an energy level of electrons of a specific observation object substance to an excitation level by means of the excitation light (one-photon absorption). At this time, when the sample 20 is a sample containing a fluorescent substance (fluorescent sample), a spontaneously emitted light (fluorescence) at the optical frequency $\omega_2$ is generated from the sample 20.

Further, the wavelength selection filter 22 of this embodiment includes wavelength-selectivity characteristics that cause the wavelength selection filter 22 to allow a light at the optical frequency $\omega_1$ to pass therethrough and block a light at the optical frequency $\omega_2$ provided thereto. Therefore, in this embodiment, the fluorescence at the optical frequency $\omega_2$ is not incident on the light detector 24, but the excitation light at the optical frequency $\omega_1$ is incident on the light detector 24.

Further, the intensity of the excitation light in this embodiment is set to an appropriate value so as to cause the light absorption amount in the central region $A_2$ of the light spot S to be saturated and prevent the light absorption amount in the peripheral region $A_1$ of the light spot S from being saturated.

Figure 9:
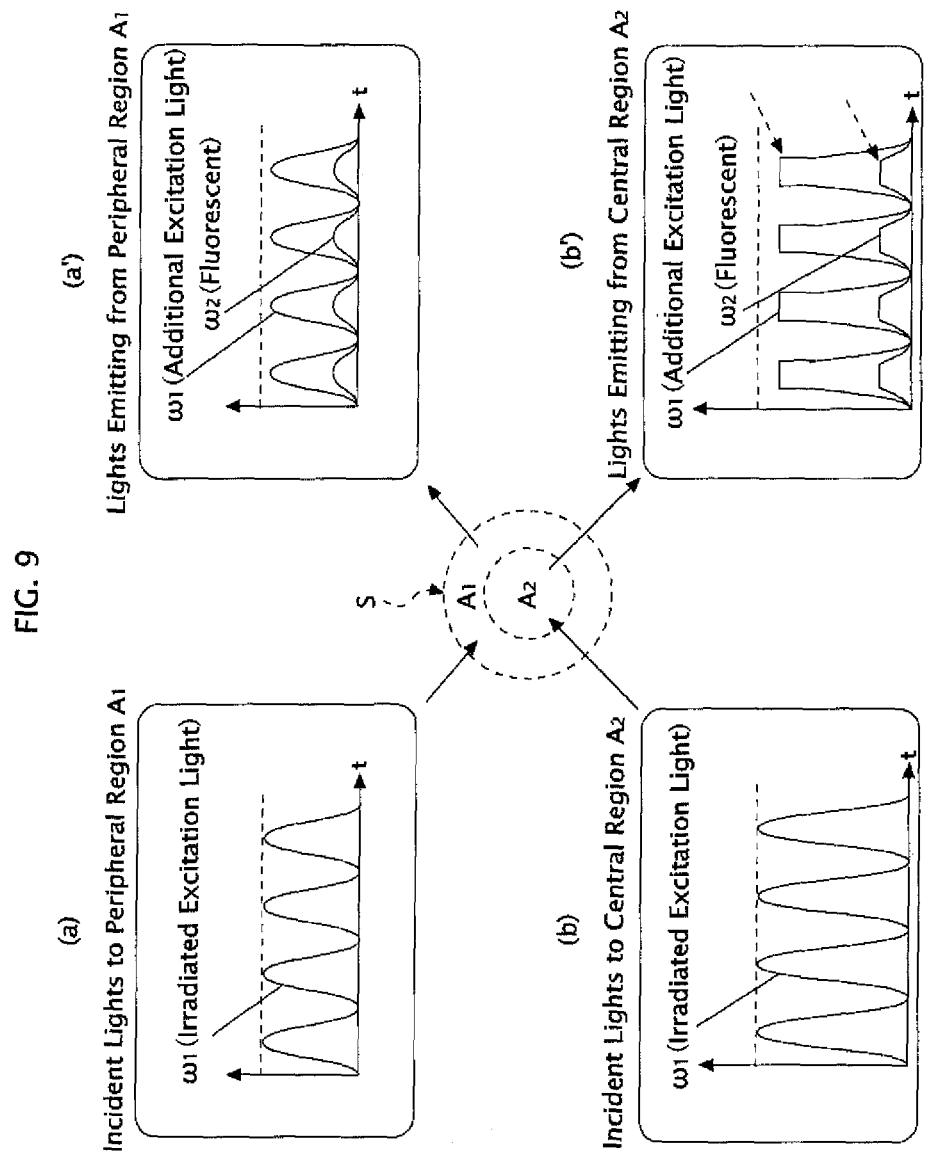
FIG. 9 is a diagram comparing a light incident on respective regions of the light spot S and respective lights emitted from the respective regions in the fourth embodiment.

FIG. 9 illustrates time-variable waveforms of respective lights in this embodiment. In this embodiment as well, a high-frequency component over the frequency $f_m$ is not generated in the additional excitation light and the fluorescent emitting from the peripheral region $A_1$ as illustrated in the part (a') of FIG. 9, whereas a high-frequency component over the frequency $f_m$ is generated in the additional excitation light and the fluorescent emitting from the central region $A_2$ as illustrated in the part (b') of FIG. 9.

Accordingly, in a signal to be detected by the lock-in amplifier 25 in this embodiment, the light absorption amount in the peripheral region $A_1$ is not reflected, but the light absorption amount in the central region $A_2$ is reflected.

Accordingly, in this embodiment as well, a super-resolution observation of the sample 20 is enabled similarly to the first embodiment.

Modified Example of Fourth Embodiment

Note that in this embodiment, the detection frequency of lock-in detection performed by the lock-in amplifier 25 is set to the double ($2f_m$) of the modulation frequency $f_m$, but it may be set to another value larger than the modulation frequency $f_m$. For example, the detection frequency may be set to $N \times f_m$, (where N is an integer of 2 or more). By increasing the detection frequency as above, the super-resolution effect can be further increased. This is because a region that can be a generation origin of the high-frequency component out of the light spot S is limited only to a region with a particularly high light intensity, namely only to an extremely narrow region. Thereby, the higher the detection frequency is, the more the super-resolution effect increases.

Further, in the super-resolution microscopy of this embodiment, a light at the optical frequency $\omega_2$ is not irradiated to the sample 20, and thus components for leading the light at the optical frequency $\omega_2$ to the sample 20 (the CW laser light source 11-2, the lens 12-2, the mirror M2, the dichroic mirror 134, and the like) may be omitted.

Further, although in the super-resolution microscopy of this embodiment, the sample 20 is assumed as a fluorescent sample, even if the sample 20 is a sample not containing a fluorescent substance (non-fluorescent sample), a super-resolution observation on the sample 20 can be performed by detecting the additional excitation light.

Fifth Embodiment

Hereinafter, there will be explained a super-resolution microscopy utilizing a two-photon absorption process as a fifth embodiment of the present invention. Here, only differences from the first embodiment are explained.

Figure 10:
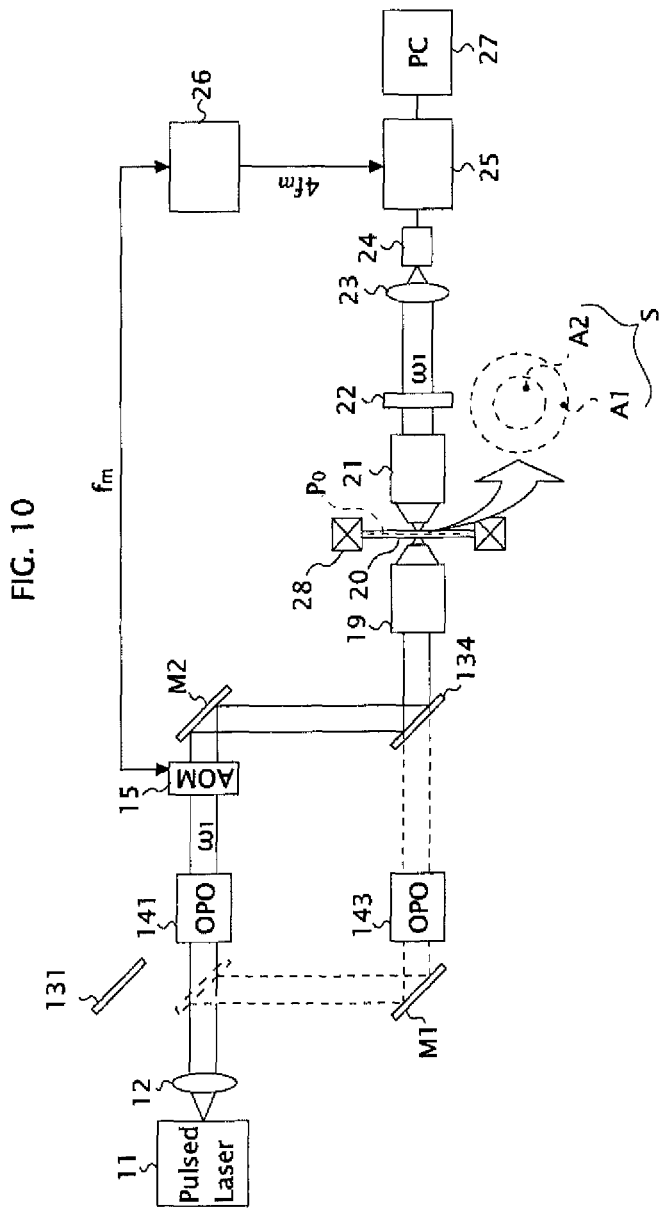
FIG. 10 is a configuration diagram of a super-resolution microscopy of a fifth embodiment.

FIG. 10 is a configuration diagram of the super-resolution microscopy of this embodiment. As illustrated in FIG. 10, the super-resolution microscopy of this embodiment is that the pulsed laser light at the optical frequency $\omega_2$ heading toward the observation object plane $P_0$ in the super-resolution microscopy of the first embodiment is turned off. In this embodiment, only the pulsed laser light at the frequency $\omega_1$ is used as the excitation light. Note that in order to turn off the pulsed laser light at the optical frequency $\omega_2$ heading toward the observation object plane $P_0$, for example, the beam splitter 131 only needs to be displaced from the optical path as illustrated in the upper left of FIG. 10.

Further, in this embodiment, a combination of the intensity of the excitation light and the optical frequency $\omega_1$ is set so as to cause the two-photon absorption process to occur in the observation object substance existing in the light spot S. The optical frequency $\omega_1$ is desirably set to be within a range of from visible region to near-infrared region wavelengths approximately in terms of a wavelength.

The two-photon absorption process is a process of shifting an energy level of electrons of a specific observation object substance to a high excitation level by means of the excitation light (two-photon absorption). At this time, when the sample 20 is a sample containing a fluorescent substance (fluorescent sample), a spontaneously emitted light (fluorescence) at the optical frequency $\omega_2$ is generated from the sample 20.

Further, the wavelength selection filter 22 of this embodiment includes wavelength-selectivity characteristics that cause the wavelength selection filter 22 to allow a light at the optical frequency $\omega_1$ to pass therethrough and block a light at the optical frequency $\omega_2$ provided thereto. Therefore, in this embodiment, the fluorescence at the optical frequency $\omega_2$ is not incident on the light detector 24, but the excitation light at the optical frequency $\omega_1$ is incident on the light detector 24.

Further, the intensity of the excitation light in this embodiment is set to an appropriate value so as to cause the light absorption amount in the central region $A_2$ of the light spot S to be saturated and prevent the light absorption amount in the peripheral region $A_1$ of the light spot S from being saturated.

Further, the detection frequency of the lock-in amplifier 25 of this embodiment is set to not the double but the quadruple ($4f_m$) of the modulation frequency $f_m$ of the excitation light.

FIG. 11 illustrates time-variable waveforms of respective lights in this embodiment. In this embodiment, as illustrated in the part (a') of FIG. 11, a time-variable waveform I(r) of the fluorescent emitting from the peripheral region $A_1$ of the light spot S is expressed by $I(t)=(1+\cos 2\pi f_m t)^2$. Therefore, in this embodiment, as illustrated in the part (a') of FIG. 11, a frequency component at the frequency $2f_m$ is generated in each of the additional excitation light and the fluorescence emitting from the peripheral region $A_1$.

However, in this embodiment, a high-frequency component over the frequency $2f_m$ is not generated in the additional excitation light and the fluorescence emitting from the peripheral region $A_1$ as illustrated in the part (a') of FIG. 11, whereas a high-frequency component over the frequency $2f_m$ is generated in each of the additional excitation light and the fluorescence emitting from the central region $A_2$ as illustrated in the part (b') of FIG. 11.

Accordingly, in a signal to be detected by the lock-in amplifier 25 in this embodiment, the light absorption amount in the peripheral region $A_1$ is not reflected, but the light absorption amount in the central region $A_2$ is reflected.

Accordingly, in this embodiment as well, a super-resolution observation of the sample 20 is enabled similarly to the first embodiment.

Modified Example of Fifth Embodiment

Note that in this embodiment, the detection frequency of lock-in detection performed by the lock-in amplifier 25 is set to the quadruple ($4f_m$) of the modulation frequency $f_m$, but it may be set to another value larger than the modulation frequency $2f_m$. For example, the detection frequency may be set to $N \times f_m$, (where N is an integer of 2 or more). By increasing the detection frequency as above, the super-resolution effect can be further increased. This is because a region that can be a generation origin of the high-frequency component out of the light spot S is limited only to a region with a particularly high light intensity, namely only to an extremely narrow region. Thereby, the higher the detection frequency is, the more the super-resolution effect increases.

Further, although in the super-resolution microscopy of this embodiment, the sample 20 is assumed as a fluorescent sample, even if the sample 20 is a sample not containing a fluorescent substance (non-fluorescent sample), a super-resolution observation on the sample 20 can be performed by detecting the additional excitation light.

Further, although in the super-resolution microscopy of this embodiment, only the excitation light at the optical frequency $\omega_1$ is used in order to cause the two-photon absorption process to occur, both the first excitation light at the optical frequency $\omega_1$ and the second excitation light at the optical frequency $\omega_2$ may be used. In the case, the light intensity of the first excitation light may be modulated by means of the modulation frequency $f_m$, and the first excitation light or second excitation light emitted from the sample 20 may be lock-in detected by means of the detection frequency $2N \times f_m$, (where N is an integer of 2 or more).

Note that when in the super-resolution microscopy of this embodiment, a light at the optical frequency $\omega_2$ is not emitted to the sample 20, components for leading the light at the optical frequency $\omega_2$ to the sample 20 (the beam splitter 131, the mirror M1, the optical parametric oscillator 143, the mirror M2, the dichroic mirror 134, and the like) may be omitted.

Supplements of Embodiments and Modified Examples

Note that although in one of the above-described embodiments or modified examples, an improvement in resolving power in the plane perpendicular to the optical axis is explained, a resolving power in the optical axis direction also improves similarly. This is because the aforementioned generation origin of the high-frequency component is limited only to the vicinity of a collecting point with a high light intensity in the optical axis direction as well as in the plane perpendicular to the optical axis. That is, in one of the above-described embodiments or modified examples in which a high-frequency component due to saturation is detected, the resolving power improves over both the direction perpendicular to the optical axis and the optical axis direction, in other words, over three-dimensional directions of x, y, and z.

Note that although in the first embodiment, the second embodiment, the fifth embodiment, and their modified examples, a combination of a single laser light source and two optical parametric oscillators is used in order to generate two pulsed laser lights with different optical paths, a combination of a single laser light source and a single optical parametric oscillator may be used. In the case, however, as one of two pulsed laser lights, a laser light emitted from the laser light source is used as it is. Further, in the case, a repetition frequency of one of two pulsed laser lights and a repetition frequency of the other of them are desirably synchronized.

Note that although in the first embodiment, the second embodiment, the fifth embodiment, and their modified examples, the saturation of absorption by means of the light at the optical frequency $\omega_1$ (a saturation phenomenon) is explained, a saturation phenomenon by means of the light at the optical frequency $\omega_2$ may be utilized.

Further, although in one of the above-described embodiments or one of the above-described modified examples, one of the stimulated emission process, the ESA process, the GSD process, the one-photon absorption process, and the two-photon absorption process is caused to occur as the optical process accompanying the light absorption of the observational object substance, another optical process accompanying the light absorption of the observation object substance may be caused to occur.

Further, although in one of the above-described embodiments or one of the above-described modified examples, the sample 20 is assumed as a fluorescent sample, the sample 20 may be a sample not containing a fluorescent substance (non-fluorescent sample). Accordingly, the present invention is applicable not only to the bio-observation but also to other various observations such as material observation, for example.

Further, although in one of the above-described embodiments or one of the above-described modified examples, only one kind of optical process is caused to occur as the optical process accompanying the light absorption of the observation object substance, such a single super-resolution microscopy as to be capable of causing two or more kinds of optical processes different mutually to occur, namely such a super-resolution microscopy as to be capable of performing mode switching among/between a plurality of different modes of an optical process may be configured. Note that in the super-resolution microscopy capable of performing mode switching, for example, functions (1) to (5) below are mounted.

(1) A function of adjusting a time-variable waveform of a light to be emitted to the sample 20

(2) A function of adjusting each of the optical frequency $\omega_1$ and the optical frequency $\omega_2$ (3) A function of turning on/off at least one of the light at the optical frequency $\omega_1$ to be emitted to the sample 20 and the light at the optical frequency $\omega_2$ to be emitted to the sample 20

(4) A function of adjusting the detection frequency of the lock-in amplifier 25

(5) A function of switching the wavelength selection filter 22 among/between a plurality of wavelength selection filters different in a selection wavelength Further, although in one of the above-described embodiments or modified examples, the transmission-type microscopy is explained, the present invention is applicable also to a reflection-type microscopy.

Further, although in one of the above-described embodiments or modified examples, the "intensity," which is one kind of property of the light at the optical frequency $\omega_1$, is modulated, in place of the intensity of the light at the optical frequency $\omega_1$, another property of the light at the optical frequency $\omega_1$, for example, one of a phase, polarization, and an optical frequency may be modulated.

Further, although in one of the above-described embodiments or modified examples, the property of only one of the light at the optical frequency $\omega_1$ and the light at the optical frequency $\omega_2$ is modulated, both properties of the light at the optical frequency $\omega_1$ and the light at the optical frequency $\omega_2$ may be modulated by means of modulation frequencies different from each other.

Operation and Effect of Embodiments

The super-resolution observation device (super-resolution microscopy) of one of the above-described embodiments includes an illumination optical system (the objective lens 19) that focus a first illuminating light at an optical frequency $\omega_1$ and a second illuminating light at an optical frequency $\omega_2$ on a region (the light spot S) of an observation object plane ($P_O$); a modulation unit (the acousto-optics modulator 15) that uses a modulation frequency $f_m$ to modulate a property of the first illuminating light heading toward the region (light spot S); and an extraction unit (the lock-in amplifier 25, the signal generator 26, and the wavelength selection filter 22) that extracts, from lights generated in the region (light spot S) in response to the first illuminating light and the second illuminating light, a component at the optical frequency $\omega_1$ or $\omega_2$, the component of which the property changes at a frequency that is higher than the modulation frequency $f_m$.

Note that the property being an object modulated by the modulation unit is one of an intensity, a phase, polarization, and an optical frequency of the first illuminating light.

Further, in the super-resolution observation device (super-resolution microscopy) of the first embodiment, a combination of an intensity of the first illuminating light, an intensity of the second illuminating light, the optical frequency $\omega_1$, and the optical frequency $\omega_2$ is set so as to cause a stimulated emission process to occur in an observation object substance in the region (light spot S) and cause a light absorption amount of the observation object substance by means of the stimulated emission process to be saturated only in a portion of the region.

Further, in the super-resolution observation device (super-resolution microscopy) of the second embodiment, a combination of an intensity of the first illuminating light, an intensity of the second illuminating light, the optical frequency $\omega_1$, and the optical frequency $\omega_2$ is set so as to cause an excited-state absorption process to occur in an observation object substance in the region (light spot S) and cause a light absorption amount of the observation object substance by means of the excited-state absorption process to be saturated only in a portion of the region.

Further, in the super-resolution observation device (super-resolution microscopy) of the third embodiment, a combination of an intensity of the first illuminating light, an intensity of the second illuminating light, the optical frequency $\omega_1$, and the optical frequency $\omega_2$ is set so as to cause a ground state depletion process to occur in an observation object substance in the region (light spot S) and cause a light absorption amount of the observation object substance by means of the ground state depletion process to be saturated only in a portion of the region.

In the super-resolution observation device (super-resolution microscopy) of one of the first embodiment to the third embodiment, an object extracted by the extraction unit (lock-in amplifier 25, signal generator 26, and wavelength selection filter 22) is a component of which the property changes at a frequency $N \times f_m$, for example, (where N is an integer of 2 or more).

Further, in the super-resolution observation device (super-resolution microscopy) of the fourth embodiment, emission of the second illuminating light to the region (light spot) is omitted, a combination of an intensity of the first illuminating light and the optical frequency $\omega_1$ is set so as to cause a one-photon absorption process to occur in an observation object substance in the region (light spot) and cause a light absorption amount of the observation object substance by means of the one-photon absorption process to be saturated only in a portion of the region, and an object extracted by the extraction unit (lock-in amplifier 25, signal generator 26, and wavelength selection filter 22) is a component at the optical frequency $\omega_1$, the component of which the property changes at a frequency that is higher than the modulation frequency $f_m$.

Further, in the super-resolution observation device (super-resolution microscopy) of the fifth embodiment, emission of the second illuminating light to the region (light spot) is omitted, a combination of an intensity of the first illuminating light and the optical frequency $\omega_1$ is set so as to cause a two-photon absorption process to occur in an observation object substance in the region (light spot) and cause a light absorption amount of the observation object substance by means of the two-photon absorption process to be saturated only in a portion of the region, and an object extracted by the extraction unit (lock-in amplifier 25, signal generator 26, and wavelength selection filter 22) is a component at the optical frequency $\omega_1$, the component of which the property changes at a frequency that is higher than the modulation frequency $f_m$.

According to the present invention, the super-resolution observation device and the super-resolution observation method that are capable of performing a super-resolution observation on a sample without staining the sample are realized.

The many features and advantages of the embodiment are apparent from the detailed specification and, thus it is intended by the appended claims to cover all such features and advantages of the embodiment that fall within the true spirit and scope thereof. Further, since numerous modifications and changes will readily occur to those skilled in the art, it is not desired to limit the inventive embodiment to the exact construction and operation illustrated and described, and accordingly all suitable modifications and equivalents may be resorted to, falling within the scope thereof.

What is claimed is:

1. A super-resolution observation device, comprising:
   an illumination optical system focusing a first illuminating light at optical frequency $\omega_1$ which shifts an energy level of electrons of an observation object substance being specific to an excitation level and a second illuminating light at optical frequency $\omega_2$ which shifts excited electrons of the observation object substance to a ground state to generate a stimulated emission light on a region of an observation object plane of the observation object substance;

a modulation unit modulating a property of the first illuminating light heading toward the region at a modulation frequency $f_m$; and an extraction unit extracting a component at one of the optical frequency $\omega_1$ and the optical frequency $\omega_2$ from a light generated in the region according to the first illuminating light and the second illuminating light, the component of which the property changes at a frequency higher than the modulation frequency $f_m$.

2. The super-resolution observation device according to claim 1, wherein the property of a modulation object of the modulation unit is one of intensity, a phase, polarization, and an optical frequency of the first illuminating light.

3. The super-resolution observation device according to claim 1, wherein a combination of intensity of the first illuminating light, intensity of the second illuminating light, the optical frequency $\omega_1$, and the optical frequency $\omega_2$ is set so as to occur a stimulated emission process in the observation object substance in the region and to saturate a light absorption amount of the observation object substance through the stimulated emission process only in a portion of the region.

4. The super-resolution observation device according to claim 3, wherein an extraction object of the extraction unit is a component of which the property changes at a frequency $N \times f_m$ (where N is an integer of 2 or more).

5. The super-resolution observation device according to claim 1, wherein a combination of intensity of the first illuminating light, intensity of the second illuminating light, the optical frequency $\omega_1$, and the optical frequency $\omega_2$ is set so as to occur an excited-state absorption process in the observation object substance in the region and to saturate a light absorption amount of the observation object substance through the excited-state absorption process only in a portion of the region.

6. The super-resolution observation device according to claim 1, wherein a combination of intensity of the first illuminating light, intensity of the second illuminating light, the optical frequency $\omega_1$, and the optical frequency $\omega_2$ is set so as to occur a ground state depletion process in the observation object substance in the region and to saturate a light absorption amount of the observation object substance through the ground state depletion process only in a portion of the region.

7. The super-resolution observation device according to claim 1, wherein:

irradiation of the second illuminating light to the region is omitted;

a combination of intensity of the first illuminating light and the optical frequency $\omega_1$ is set so as to occur a one-photon absorption process in the observation object substance in the region and to saturate a light absorption amount of the observation object substance through the one-photon absorption process only in a portion of the region; and an extraction object of the extraction unit is a component at the optical frequency $\omega_1$, the component of which the property changes at a frequency higher than the modulation frequency $f_m$.

8. The super-resolution observation device according to claim 1, wherein:

irradiation of the second illuminating light to the region is omitted;

a combination of intensity of the first illuminating light and the optical frequency $\omega_1$ is set so as to occur a two-photon absorption process in the observation object substance in the region and to saturate a light absorption amount of the observation object substance through the two-photon absorption process only in a portion of the region; and an extraction object of the extraction unit is a component at the optical frequency $\omega_1$, the component of which the property changes at a frequency higher than the modulation frequency $f_m$.

9. The super-resolution observation device according to claim 1, wherein the first illuminating light and the second illuminating light are irradiated to the observation object plane so that a time difference between a timing at which a pulse of the first illuminating light reaches the observation object plane and a timing at which a pulse of the second illuminating light reaches the observation object plane will occur.

10. The super-resolution observation device according to claim 1, wherein an optical path length adjusting mechanism is provided in at least one optical path of an independent optical path of the first illuminating light and an independent optical path of the second illuminating light.

11. The super-resolution observation device according to claim 1, wherein the first illuminating light and the second illuminating light have a wavelength difference of 3600 cm$^{-1}$ or more in terms of energy.

12. A super-resolution observation device, comprising:

an illumination optical system focusing an illuminating light at optical frequency $\omega_1$ which shifts an energy level of electrons of an observation object substance being specific to an excitation level on a region of an observation object plane of the observation object substance;

a modulation unit modulating a property of the illuminating light heading toward the region at a modulation frequency $f_m$; and an extraction unit extracting a component at the optical frequency $\omega_1$ from a light generated in the region according to the illuminating light, the component of which the property changes at a frequency higher than the modulation frequency $f_m$.

13. A super-resolution observation method, comprising:

focusing a first illuminating light at optical frequency $\omega_1$ which shifts an energy level of electrons of an observation object substance being specific to an excitation level and a second illuminating light at optical frequency $\omega_2$ which shifts excited electrons of the observation object substance to a ground state to generate a stimulated emission light on a region of an observation object plane of the observation object substance;

modulating a property of the first illuminating light heading toward the region at a modulation frequency $f_m$; and extracting a component at one of the optical frequency $\omega_1$ and the optical frequency $\omega_2$ from a light generated in the region according to the first illuminating light and the second illuminating light, the component of which the property changes at a frequency higher than the modulation frequency $f_m$.

14. The super-resolution observation device according to claim 13, wherein the first illuminating light and the second illuminating light are irradiated to the observation object plane so that a time difference between a timing at which a pulse of the first illuminating light reaches the observation object plane and a timing at which a pulse of the second illuminating light reaches the observation object plane will occur.

15. The super-resolution observation device according to claim 13, wherein
the first illuminating light and the second illuminating light have a wavelength difference of 3600 cm$^{-1}$ or more in terms of energy.

16. A super-resolution observation method, comprising:
focusing an illuminating light at optical frequency $\omega_1$ which shifts an energy level of electrons of an observation object substance being specific to an excitation level on a region of an observation object plane of the observation object substance;
modulating a property of the illuminating light heading toward the region at a modulation frequency $f_m$; and
extracting a component at the optical frequency $\omega_1$ from a light generated in the region according to the illuminating light, the component of which the property changes at a frequency that is higher than the modulation frequency $f_m$.

* * * * *